United States Patent [19]

Fukui et al.

[11] 4,380,534

[45] Apr. 19, 1983

[54] SOLID DRUG PREPARATIONS

[75] Inventors: Muneo Fukui, Urawa; Yutaka Konno, Omiya; Yukio Kubota, Tokyo; Masayoshi Aruga, Ageo; Hiroitsu Kawata, Kawagoe, all of Japan

[73] Assignee: Yamanouchi Pharmaceutical Co., Ltd., Tokyo, Japan

[21] Appl. No.: 249,886

[22] Filed: Apr. 1, 1981

[30] Foreign Application Priority Data

Apr. 7, 1980 [JP] Japan .................................. 55-46002

[51] Int. Cl.$^3$ ................................................ A61K 9/42
[52] U.S. Cl. ........................................................ 424/38
[58] Field of Search ....................... 424/19, 22, 38, 182

[56] References Cited

U.S. PATENT DOCUMENTS

| | | | |
|---|---|---|---|
| 2,698,822 | 1/1955 | Halpern et al. | 424/182 |
| 2,805,977 | 9/1957 | Robinson et al. | 424/38 |
| 2,875,130 | 2/1959 | Grass et al. | 424/38 |
| 2,902,407 | 9/1959 | Gross et al. | 424/38 |
| 3,035,985 | 5/1962 | Stoyle et al. | 424/38 |
| 3,037,911 | 6/1962 | Stoyle et al. | 424/38 |
| 3,078,216 | 2/1963 | Greif | 424/38 |
| 3,080,292 | 5/1963 | Koff | 424/38 |
| 3,108,046 | 10/1963 | Harbit | 424/38 |
| 3,279,998 | 10/1966 | Raff et al. | 424/38 |
| 3,538,215 | 11/1970 | Snyder et al. | 424/38 |
| 3,655,864 | 4/1972 | Grass et al. | 424/38 |
| 3,780,170 | 12/1973 | Goodhart et al. | 424/38 |
| 3,803,310 | 4/1974 | Eberlein et al. | 424/182 |
| 3,856,699 | 12/1974 | Miyano et al. | 252/316 |
| 3,960,757 | 6/1976 | Morishita et al. | 424/38 |
| 4,102,806 | 7/1978 | Kondo et al. | 252/316 |
| 4,132,753 | 1/1979 | Blichare | 264/25 |
| 4,147,768 | 4/1979 | Shaffer et al. | 424/182 |
| 4,151,273 | 4/1979 | Riegelman et al. | 424/182 X |
| 4,202,888 | 5/1980 | Eckert et al. | 424/182 |
| 4,230,702 | 10/1980 | Eckert et al. | 424/182 |

FOREIGN PATENT DOCUMENTS

| | | | |
|---|---|---|---|
| 1078283 | 3/1960 | Fed. Rep. of Germany | 424/38 |
| 1080265 | 4/1960 | Fed. Rep. of Germany | 424/38 |
| 1417326 | 10/1968 | Fed. Rep. of Germany | 424/38 |
| 41-14399 | 8/1966 | Japan | 424/38 |
| 2016922 | 9/1979 | United Kingdom | 424/38 |

Primary Examiner—Shep K. Rose
Attorney, Agent, or Firm—Burgess, Ryan and Wayne

[57] ABSTRACT

A solid microdose drug preparation containing a microdose drug such as formoterol fumarate or $\beta$-methyldigoxin coated with wax.

In the drug preparation, the stability and the content uniformity of the microdose drug have been improved.

14 Claims, No Drawings

SOLID DRUG PREPARATIONS

BACKGROUND OF THE INVENTION

1. Field of the Invention

This invention relates to a solid drug preparation containing a powder microdose drug coated with wax.

Since the drug preparation of this invention is excellent in content uniformity, it has a high practical value as a microdose drug preparation which exhibits the effect of medicine by a microdose of it. The preparation of this invention contains a stabilized drug and hence is suitable as a microdose drug preparation which does not encounter the reduction in crystallinity of an effective component therein and the reduction in the stability of the effective component during the production or storage of the preparation.

2. Description of the Prior Art

The content uniformity of a solid drug preparation gives almost no problem in a preparation having a large content of drug per unit of the preparation, i.e., a large content of drug per tablet, capsule or unit dose of the package but it becomes serious in case of a microdose drug having a drug content of less than 50 mg, particularly less than a few milligrams. For the preparation of a microdose drug, there are a practiced method (solution method) wherein a solution of a drug dissolved in a proper solvent is uniformly dispersed in excipient and then the dispersion is formed into a preparation and a method (powder dilution method) wherein a drug is compounded with an excipient in the form of the powder dilution and then the resulting product is formed into a preparation.

In the powder dilution method, since it is frequently difficult to produce drug preparations having excellent drug content uniformity by an ordinary step or, in particular, it is difficult to uniformly mix aggregates of the drug with excipients, a homogenizing step such as mixture pulverization, etc., is required and hence for obtaining a uniformity of drug content, complex manufacturing procedures are required. The solution method may be superior to the powder dilution method in the point of uniformity in drug content but in the solution method there is pointed out such difficulties that since a drug is dissolved in a solvent during the production of preparations, the crystal form changes, for example, a hydrate changes into a solvate to change the drug itself and also when the solution is dispersed in excipient, the particle size of the drug is reduced. The stability of the drug to the passage of time is thus reduced. It is very important for the preparations of extremely low dose drugs having a drug content of less than 1 mg per unit of the preparation to assure the drug content uniformity and the stability of the effective component. Since the extremely low dose drugs generally have strong medicinal activity, if the uniformity of drug content and the stability of effective component are not strictly assured, there is a possibility that the desired medicinal effect is not obtained or an unforeseen accident by overdose may occur.

SUMMARY OF THE INVENTION

As the result of various investigations to overcome such difficulties in microdose preparations, the inventors have discovered that the solid drug preparation produced by using a powder microdose drug coated with wax is excellent in the drug content uniformity and in the stability of the drug.

The present invention provides a solid drug preparation containing a powder microdose drug coated with wax.

DESCRIPTION OF THE PREFERRED EMBODIMENT

According to this invention, microdose drugs are coated with wax and hence even aggregates of drugs are fixed in a well-dispersed form. As a result, solid drug preparations having excellent drug content uniformity are obtained even by the simple manufacturing procedures, e.g., the direct compression method. Also, when the powdered drug coated with wax is used, the surface property of the drug can be masked and hence the loss of the drug by electrostatic or stickily attaching of the drug can be prevented. Even if the absolute amount of the loss is small, the influence of the loss expressed in percent of the calculated amount is large and hence the loss of the drug cannot be overlooked in case of the microdose preparations.

The microdose preparation in this invention means an extremely low dose preparation which contains an active component less than 5 mg, in particular less than 1 mg per unit of the preparation. Examples of such drugs used in this invention are digoxin, digitoxin, $\beta$-methyldigoxin, formoterol fumarate, procathelol, dexamethasone, $\beta$-methasone, nitroglycerin, reserpine, folic acid, cobamide, ethynylestradiol, hexoprenaline, polythiazide, diethylstilbestrol, cortisone, ergotamine, ergometrine, etc. Also, examples of waxes are fats and oils prepared by hydrogenating vegetable oils such as sesame oil, olive oil, soybean oil, corn oil, coconut oil, castor oil, etc. [e.g., hardened oils such as Lubriwax 101 and Lubriwax 102H, (the trade names, made by Freund Industrial Co., Ltd.), and Himako, (the trade name of hardened castor oil, made by Kawaken Fine Chemical Co., LTd.)]; waxes such as beeswax, carnauba wax, spermacetic, etc.; hydrocarbons such as paraffin, ceresin, etc.; fatty acids such as myristic acid, palmitic acid, stearic acid, etc.; higher alcohols such as palmitic alcohol, stearyl alcohol, etc.; polyhydric alcohols such as PEG (macrogol), batyl alcohol, etc.; and esters such as octadecyl palmitate, octadecyl stearate, etc.

The term "a powder microdose drug coated with wax" in this invention means not only powder of a microdose drug coated with wax directly or together with a definite amount of excipient but also a powder product prepared by dispersing a liquid microdose drug into wax directly or after dispersing the liquid microdose drug in a definite amount of excipient. Coating of a powder of a microdose drug with wax directly or together with a definite amount of excipient is performed by uniformly dispersing the powder into molten wax or by uniformly dispersing the powdered drug into wax dissolved in or mixed with a proper solvent and then removing the solvent by vacuum drying, spray drying, etc. In this dispersing procedure, the powder of a microdose drug of a particle size which is less than 100 $\mu$m is usually used. Also, it is performed by uniformly dispersing a liquid microdose drug into wax directly or after dispersing the drug in a definite amount of excipient. The drug coated with the wax thus obtained is then formed into a powder or granule. Of course, where the removal of the solvent is carried out by e.g. spray drying, the powdering or granulating procedure is not necessary.

The proportion of wax used is 0.05–5 times, preferably 0.3–2 times the amount of the microdose drug. As the diluting solvent, ordinary organic solvents such as methylene chloride, chloroform, carbon tetrachloride, ether, benzene, acetone, tetrahydrofuran, ethyl acetate, etc., which do not influence the property of the microdose drug are properly used solely or as a combination of them, but the solvents which do not dissolve the drug itself are preferred. There is no particular restriction on the amount of solvent used but the smallest amount thereof necessary for dissolving the wax or for mixing with the wax is suitable.

It is effective to use small amount of a surface active agent, etc. for uniformly dispersing a powder of a microdose drug into wax or increasing the adhesive property between the microdose drug and wax. As the materials used for this purpose, there are hydroxypropyl-methyl cellulose (TC-5), polyvinylpyrrolidone (PVP), $\beta$-cyclodextrin, and nonionic surface active agents (e.g., sorbitan fatty acid esters, polyoxyethylene sorbitan fatty acid esters, polyoxyethylene fatty acid esters, polyoxyethylene higher alcohol ethers, glycerol fatty acid esters, polyoxyethylene castor oil derivatives, etc.,). Also, for increasing the photostability of the microdose drug, a light shielding agent such as titanium dioxide may be used.

Powdering or granulation of the drug coated with wax is performed by dispersing the drug into wax mechanically or by ultrasonic treatment under heating, if necessary (under molten state of wax in case of directly dispersing the drug in the wax) and thereafter spray congealing, vacuum drying, or spray drying the dispersion.

The solid drug preparation of this invention is obtained by formulating the wax-coated powder of the drug. The production of the preparation is performed in an ordinary manner. For example, when the drug coated with wax is formulated by a simple conventional preparation step such as a direct compression method, etc., it disperses well and a preparation of excellent uniformity of the effective component can be obtained.

The effect is particularly remarkable in the preparation of microdose drugs which have a strong aggregation property. Another feature of the preparations of this invention is the good stability of the effective component. That is, in the production of the preparations of this invention, the reduction of crystallinity of the microdose drugs and the interaction between excipients and the microdose drugs can be prevented and thus the stability of drugs to the passage of time can be improved.

The dissolution properties of drugs coated with hydrophobic waxes are generally poor. The dissolution properties of drugs are influenced by the kind and amount of waxes used and also by the kind of treating solvents employed and hence the investigation of the physicochemical properties of drugs and waxes together is necessary. When the dissolution properties of drugs coated with hydrophobic waxes are poor, hydrophilic excipients may be used together for improving the properties.

Then, for proving the effects of the solid drug preparations of this invention, the following test results are shown together with the test methods.

I. The content uniformity of the drug

Test results: The tests of the content uniformity of formoterol fumarate and $\beta$-methyldigoxin were performed by the test method shown below and the results are shown in Table I.

TABLE I

| Example | Mean content % (n = 20) | Standard deviation % | Coefficient of Variation % | Max. % Min. % |
|---|---|---|---|---|
| 1 | 100.2 | 2.93 | 2.92 | 104.4 |
|  |  |  |  | 92.5 |
| 2 | 99.5 | 1.87 | 1.88 | 103.5 |
|  |  |  |  | 96.6 |
| 3 | 97.5 | 2.19 | 2.25 | 102.7 |
|  |  |  |  | 94.8 |
| 4 | 96.1 | 1.61 | 1.68 | 99.6 |
|  |  |  |  | 92.3 |
| 5 | 98.9 | 1.57 | 1.59 | 101.6 |
|  |  |  |  | 96.0 |
| 6 | 97.3 | 2.98 | 3.06 | 101.8 |
|  |  |  |  | 88.7 |
| 7 | 95.5 | 2.08 | 2.18 | 100.8 |
|  |  |  |  | 93.4 |
| 8 | 99.7 | 2.43 | 2.44 | 104.4 |
|  |  |  |  | 94.4 |
| 9 | 94.2 | 1.79 | 1.90 | 98.2 |
|  |  |  |  | 91.1 |
| 12 | 98.4 | 3.67 | 3.73 | 109.8 |
|  |  |  |  | 93.9 |
| 13 | 95.5 | 1.78 | 1.87 | 99.6 |
|  |  |  |  | 89.3 |

As shown in Table I, the coefficient of variation for formoterol fumarate and $\beta$-methyldigoxin was less than 4%, which show the good content uniformity.

Test methods:

(a). The content uniformity of the formoterol fumarate preparation (tablet) was tested by the following method.

To one tablet containing a formoterol fumarate (20 µg/tablet) was accurately added 10 ml of an aqueous solution of 0.2% sodium chloride and after heating to about 50° C. for 10 minutes, the mixture was shaken for 15 minutes. Then, the mixture was subjected to a centrifugal separation and a definite amount of the supernatant obtained was determined by means of a high-performance liquid chromatography on a column of Lichrosorb RP-18, a trade name, made by Merck & Co., Inc.

(b). The content uniformity of the $\beta$-methyldigoxin preparation (tablet) was tested by following method.

One tablet of a $\beta$-methyldigoxin preparation (100 µg/tablet) was placed in a 50 milliliter flask and after adding thereto 2.5 ml of water and allowing the mixture to stand for 10 min. to disintegrate the tablet, 40 ml of absolute ethanol was added. The mixture was immersed in an ultrasonictor for 10 min. (50 KHz, 150 Watts) and then absolute alcohol was added thereto to make up to 50 ml accurately. The solution was subjected to a centrifugal separation and accurate 1 ml of the supernatant obtained was determined according to the fluorometeric assay method described in "Yakuzai Gaku (Pharmacology)"; 37, 215(1977) by Sonobe et al.

II. Stability

Test result: The stability of formoterol fumarate to the passage of time was tested by the following test method. The results are shown in Table II.

TABLE II

| | Stability of formoterol fumarate (remaining, %) | | | |
|---|---|---|---|---|
| | Wax | Amount** | Solvent | Production method | Closed at 60° C. for 3 months |
| Control* (untreated) | — | — | — | (A) | 52.2 |
| | — | — | — | (B) | 63.8 |

TABLE II-continued

Stability of formoterol fumarate (remaining, %)

| | Wax | Amount** | Solvent | Production method | Closed at 60° C. for 3 months |
|---|---|---|---|---|---|
| Example 10 | castor wax | 50 | acetone | (B) | 82.8 |
| Example 11 | castor wax | 50 | dichloromethane | (B) | 85.1 |

*Control: Produced by the general method described in Examples 1–11 shown below.
**Amount: Weight ratio to 100 of a microdose drug.
(A): Wet granulation method.
(B): Direct compression method.

As shown in Table II, it is understood that formoterol fumarate is remarkably stabilized by the wax coating of the drug.

Test method:

The stability of a formoterol fumarate preparation (tablet) to the passage of time was tested by the following method.

The weight of 10 tablets of a formoterol fumarate preparation (20 μg/tablet) was accurately measured and after adding 18 ml of an aqueous solution of 0.2% sodium chloride and heating the mixture to about 50° C. for 10 min., the mixture was shaken for 15 min. and filtered by means of a glass filter. The residue was washed with an aqueous solution of 0.2% sodium chloride and filtered. The whole filtrates were combined with each other to make up to 25 ml accurately and then determined by the same manner as in the uniformity test described above.

III. Loss of microdose drugs during mixing procedures

Test results: The test results for the loss of formoterol fumarate during mixing procedures in case of using the wax-coated powder thereof and in case of non-coated powder thereof are shown in Table III.

TABLE III

| Number test | Wax coating | |
|---|---|---|
| | None | Coated |
| | (control) | |
| 1 | 12.0 | 1.9 |
| 2 | 10.3 | 5.3 |
| 3 | 14.9 | 2.5 |

Working condition: 18–24° C., 40–27% RH.

Test method: Each of the wax-coated powder of formoterol fumarate and the non-coated powder of formoterol fumarate obtained in Example 10 (a) shown later was mixed with crystalline lactose, pulverized into particles of less than 80 mesh to form the properly diluted powders and then the powder dilution was sieved to pass particles of less than 80 mesh. Then, the particles were mixed with crystalline lactose, crystalline cellulose (Avicel PH 102: a trade name, made by Asahi Chemicals Co., Ltd.), and potato starch using a V-type mixer and then the loss of formoterol fumarate during mixing procedures was measured. In addition, when the wax-coated powders were used, the adhesion of formoterol fumarate to the inside wall of the mixer did not occur.

The solid drug preparations of this invention are described together with the production methods by the following examples.

EXAMPLES 1–11

The solid drug preparations of this invention were produced by the following general methods.

(a). Production of the wax-coated powder:

A definite amount of wax was dissolved in 10 ml of a solvent and after suspending 1.5 g of a microdose drug in the solution, the suspension was stirred by hand. Then, after evaporating the solvent by means of a rotary evaporator, the residue was vacuum-dried for 4 hours at room temperature using phosphorus pentoxide. Then, the residue was sieved to pass the powders through 150 mesh using a brush, thereby the wax-coated powders of the microdose drug were obtained.

(b). Production of solid drug preparation (tablet):

(i) Direct compression method.

The wax-coated powders of the microdose drug obtained in step (a) were mixed with crystalline lactose pulverized into particles below 80 mesh to form properly diluted powders and the the diluted powders were sieved to pass the particles below 80 mesh. The particles were mixed with crystalline lactose, crystalline cellulose (Avicel PH 102: a trade name, made by Asahi Chemicals Co., Ltd.) and potato starch using a V-type mixer for 10 minutes and after adding thereto a proper lubricant, the mixture was formed into tablets of 6 mm diameter and 75 mg/tablet. One tablet contained 20 μg of the microdose drug.

(ii) Wet granulation method.

The wax-coated powders of the microdose drug obtained in step (a) were mixed with crystalline lactose pulverized into particles below 80 mesh to form properly diluted powders and then the diluted powders were mixed with pulverized crystalline lactose, crystalline cellulose (Avicel PH 101), and potato starch, thereby a fluidized bed granulation was performed using the potato starch paste as a binder. Then, the particles formed were dried for 30 minutes at 50° C. and sieved to pass particles through 32 mesh. Then, the particles were compounded with a proper lubricant and formed into tablets by the method shown in step (i) described above. The tablet contained 20 μg of the microdose drug.

Practical examples of this invention are shown in the following table.

| Example | Microdose drug | (a) Production of wax-coated powder | | | (b) Production of solid drug preparation (tablet) |
|---|---|---|---|---|---|
| | | Wax | Amount* | Solvent | |
| 1 | formoterol fumarate | Lubriwax 102 H | 5 | dichloromethane | (B) |
| 2 | formoterol fumarate | Lubriwax 102 H | 5 | " | (A) |
| 3 | formoterol fumarate | Lubriwax 102 H | 30 | " | (B) |
| 4 | formoterol fumarate | Lubriwax 102 H | " | " | (A) |
| 5 | formoterol | Lubriwax | 200 | " | (B) |

-continued

| Example | Microdose drug | (a) Production of wax-coated powder | | | (b) Production of solid drug preparation (tablet) |
|---|---|---|---|---|---|
| | | Wax | Amount* | Solvent | |
| | fumarate | 102 H | | | |
| 6 | formoterol fumarate | Lubriwax 101 | 100 | acetone | (B) |
| 7 | formoterol fumarate | Lubriwax 101 | 100 | " | (A) |
| 8 | formoterol fumarate | castor wax | 100 | " | (B) |
| 9 | formoterol fumarate | " | 100 | " | (A) |
| 10 | formoterol fumarate | " | 50 | " | (B) |
| 11 | formoterol fumarate | " | 50 | dichloromethane | (B) |

Amount*: Weight ratio to 100 of the microdose drug.
(A): Wet granulation method;
(B): Direct compression method

EXAMPLE 12

(a) Production of wax-coated powder of β-methyldigoxin:

In a 100 milliliter eggplant type flask was placed 1.5 g of Lubriwax 102H (a trade name, made by Freund Industrial Co., Ltd.) and the wax was dissolved in 50 ml of a carbon tetrachloride solution of 0.5% polyoxyethylene castor oil derivative HCO-60 (a trade name, made by Nikko Chemicals Co., Ltd.) under heating. In the solution was suspended 1.5 g of β-methyldigoxin and the flask was immersed in an ultrasonicator for 5 min. at 50 KHz and 150 watts, whereby a good suspension was obtained. (Note: When HCO-60 was not added, the aggregation of β-methyldigoxin occured greatly). The suspension was distilled by means of a rotary evaporator to remove the solvent and after drying the residue at 4 hours under reduced pressure at room temperature using phosphorus pentoxide, the product was sieved to pass particles through 150 mesh, whereby the wax-treated product of β-methyldigoxin was obtained.

(b) Production of β-methyldigoxin tablets by direct compression method:

The wax-treated product of β-methyldigoxin obtained in step (a) described above was mixed with crystalline lactose pulverized into particles below 80 mesh to form a properly diluted powders and the diluted powders were sieved to pass particles through 80 mesh. The particles were then mixed with crystalline lactose, crystalline cellulose (Avicel PH 102), and corn starch by means of a V-type mixer and after adding thereto proper lubricant, the mixture was formed into tablets of 7 mm diameter and 120 mg/tablet. The tablet contained 100 μg of β-methyldigoxin.

EXAMPLE 13

(a) The wax-coated powder of β-methyldigoxin was produced by the same manner as in Example 12 (a) described above.

(b) Production of β-methyldigoxin tablets by wet granulation method:

The wax-treated powder of β-methyldigoxin obtained in step (a) described above was mixed with crystalline lactose pulverized to particles below 80 mesh to form properly diluted powders and then the diluted powders were subjected to a fluidized bed granulation using 2% potato starch paste as a binder. The granules obtained were dried for 30 min. at 50° C., sieved to pass particles through 32 mesh, and after mixing with a proper lubricant, the mixture was formed into tablets by the manner shown in Example 12 (b). The tablet contained 100 μg of β-methyldigoxin.

What is claimed is:

1. In a solid pharmaceutical composition containing less than 5 mg/dosage unit of a powdered microdose drug subject to changes in crystal form stability selected from the group consisting of gidoxin, digitoxin, β-methyl-digoxin, formoterol fumarate, procathelol, dexamethasone, β-methasone, nitroglycerin, reserpine, folic acid, cobamide, ethynylestradiol, hexoprenaline, polythiazide, diethylstilbestrol, cortisone, ergotamine, and ergometrine, the improvement comprising said powdered microdose drug being coated with a hydrophobic wax by the method comprising uniformly dispersing a powder of a microdose drug directly in molten wax and forming a powder or granule of the dispersion, or dispersing a powder of a microdose drug in a hydrophobic wax dissolved in a solvent, removing the solvent and forming a powder or granule of the residue, whereby said powdered microdose drug is stabilized against changes in crystallinity and against losses due to electrostatic charge or stickiness.

2. The composition as claimed in claim 1 wherein the amount of the microdose drug is less than 1 mg/dosage unit of the preparation.

3. The composition as claimed in claim 1 or 2 wherein the proportion of the hydrophobic wax in the hydrophobic wax-coated drug is 0.05–5 parts by weight per 1 part by weight of the microdose drug.

4. The composition as claimed in claim 3 wherein the hydrophobic wax is a hydrogenated oil.

5. The composition as claimed in claim 3 wherein the microdose drug is formoterol fumarate or β-methyldigoxin.

6. The composition as claimed in claim 5 wherein the microdose drug is formoterol fumarate.

7. The composition as claimed in claim 5 wherein the microdose drug is β-methyldigoxin.

8. The composition as claimed in claim 1 or 2 wherein the hydrophobic wax is a hydrogenated oil.

9. The composition as claimed in claim 8, wherein the microdose drug is formoterol fumarate or β-methyldigoxin.

10. The composition as claimed in claim 9 wherein the microdose drug is formoterol fumarate.

11. The composition as claimed in claim 1 or 2 wherein the microdose drug is formoterol fumarate or β-methyldigoxin.

12. The composition as claimed in claim 11 wherein the microdose drug is formoterol fumarate.

13. The composition as claimed in claim 11 wherein the microdose drug is β-methyldigoxin.

14. The composition as claimed in claim 1 or 2 wherein the step of forming a powder is performed by spray congealing, vacuum drying, or spray drying.

* * * * *